(12) United States Patent
Dixon et al.

(10) Patent No.: US 10,512,774 B2
(45) Date of Patent: Dec. 24, 2019

(54) CLOSED-LOOP HYBRID ORTHOTIC SYSTEM FOR REHABILITATION AND FUNCTIONAL MOBILITY ASSISTANCE

(71) Applicant: University of Florida Research Foundation, Incorporated, Gainesville, FL (US)

(72) Inventors: Warren Dixon, Gainesville, FL (US); Matthew J. Bellman, Gainesville, FL (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 763 days.

(21) Appl. No.: 15/105,149

(22) PCT Filed: Dec. 18, 2014

(86) PCT No.: PCT/US2014/071309
§ 371 (c)(1),
(2) Date: Jun. 16, 2016

(87) PCT Pub. No.: WO2015/095611
PCT Pub. Date: Jun. 25, 2015

(65) Prior Publication Data
US 2016/0310731 A1 Oct. 27, 2016

Related U.S. Application Data

(60) Provisional application No. 61/917,586, filed on Dec. 18, 2013.

(51) Int. Cl.
*A61N 1/36* (2006.01)
*A61F 5/01* (2006.01)
(Continued)

(52) U.S. Cl.
CPC ........ *A61N 1/36003* (2013.01); *A61F 5/0125* (2013.01); *A61F 5/0127* (2013.01);
(Continued)

(58) Field of Classification Search
CPC .... A61N 1/36003; A61H 3/00; A61H 1/0237; A61H 1/024; A61H 1/0255;
(Continued)

(56) References Cited

U.S. PATENT DOCUMENTS

| 5,121,747 A | 6/1992 | Andrews |
|---|---|---|
| 5,507,788 A | 4/1996 | Lieber |

(Continued)

FOREIGN PATENT DOCUMENTS

| CN | 2654173 Y | 11/2004 |
|---|---|---|
| CN | 101244753 A2 | 8/2008 |

(Continued)

OTHER PUBLICATIONS

EP15811103.9, Dec. 12, 2017, Extended European Search Report.
(Continued)

*Primary Examiner* — Keri J Nelson
(74) *Attorney, Agent, or Firm* — Alston & Bird LLP

(57) ABSTRACT

Hybrid orthotic devices configured to apply electrical stimulation to one or more body parts of a person are generally described. A hybrid orthotic device may comprise one or more sensors, one or more electrodes, and a controller configured to receive input signals from the one or more sensors and deliver output signals to the one or more electrodes. In certain cases, the controller may be configured to store one or more programs associated with functional activities (e.g., standing, sitting, and/or walking), and the programs may be configured to enable one or more body parts of the person to track a desired trajectory. In some embodiments, a program may implement a Robust Integral (Continued)

of the Sign of the Error (RISE) control method. The program may further implement control methods to compensate for electromechanical delay and/or muscle fatigue. In certain embodiments, a program may further implement neural network (NN)-based methods.

28 Claims, 6 Drawing Sheets

(51) Int. Cl.
 *A61H 3/00* (2006.01)
 *A61H 1/02* (2006.01)
(52) U.S. Cl.
 CPC ............... *A61H 1/024* (2013.01); *A61H 3/00* (2013.01); *A61H 2201/164* (2013.01); *A61H 2201/5005* (2013.01); *A61H 2201/5007* (2013.01)
(58) Field of Classification Search
 CPC .......... A61H 1/0262; A61H 2201/5005; A61H 2201/5007; A61F 5/0123; A61F 5/0125; A61F 5/0127
 USPC ............ 607/48–49; 601/5, 15; 602/2, 23, 26
 See application file for complete search history.

(56) References Cited

U.S. PATENT DOCUMENTS

| | | | |
|---|---|---|---|
| 5,980,435 | A | 11/1999 | Joutras et al. |
| 7,190,141 | B1 | 3/2007 | Ashrafiuon et al. |
| 7,280,871 | B2 | 10/2007 | Davis et al. |
| 7,497,806 | B2 | 3/2009 | Duncan et al. |
| 8,249,714 | B1 | 8/2012 | Hartman et al. |
| 8,620,438 | B1 | 12/2013 | Wijting et al. |
| 2003/0083596 | A1 | 5/2003 | Kramer et al. |
| 2003/0093012 | A1 | 5/2003 | Smyser et al. |
| 2003/0093021 | A1* | 5/2003 | Goffer ................... A61F 5/0102 602/23 |
| 2004/0172097 | A1 | 9/2004 | Brodard et al. |
| 2006/0247095 | A1 | 11/2006 | Rummerfield |
| 2007/0208392 | A1 | 9/2007 | Kuschner et al. |
| 2009/0018612 | A1 | 1/2009 | Duncan et al. |
| 2013/0331911 | A1 | 12/2013 | King et al. |
| 2017/0157396 | A1 | 6/2017 | Dixon et al. |

FOREIGN PATENT DOCUMENTS

| | | |
|---|---|---|
| CN | 101244753 A4 | 8/2008 |
| EP | 1 552 492 A2 | 7/2005 |
| JP | 2003-117006 A | 4/2003 |
| WO | WO 03/105744 A2 | 12/2003 |

OTHER PUBLICATIONS

Extended European Search Report for European Application No. EP 15811103.9 dated Dec. 12, 2017.
International Search Report and Written Opinion dated Apr. 17, 2015 for Application No. PCT/US2014/071309.
Invitation to Pay Additional Fees dated Nov. 17, 2015 for Application No. PCT/US2015/034562.
International Search Report and Written Opinion dated Feb. 1, 2016 for Application No. PCT/US2015/034562.
[No Author Listed], About Us. Restorative Therapies: The Leader in FES Powered Systems. http://www.restorative-therapies.com/about-us [last accessed Aug. 11, 2016]. 4 pages.
Andrews et al., Hybrid FES orthosis incorporating closed loop control and sensory feedback. J Biomed Eng. Apr. 1988;10(2):189-95.
Bellman et al., Automatic Control of Cycling Induced by Functional Electrical Stimulation with Electric Motor Assistance. IEEE Trans Aut Sci Eng. Feb. 29, 2016. Manuscript. 8 pages.
Bellman et al., Stationary Cycling Induced by Switched Functional Electrical Stimulation Control. arXiv:1309.7937v3. Mar. 13, 2014. 8 pages.
Bellman et al., Switched Control of Cadence During Stationary Cycling Induced by Functional Electrical Stimulation. IEEE Trans Neur Sys Rehab Eng. Nov. 13, 2015. [Epub ahead of print]. 11 pages.
Berkelmans et al., The development of a hybrid outdoor FES bike. 8th Annual Conference of the International FES Society. Maroochydore, Queensland. Jul. 2003. 2 pages.
Bhatia et al., State of art: Functional Electrical Stimulation (FES). Int J Biomed Eng Tech. Feb. 8, 2011;5(1):77-99.
Dai et al., Application of tilt sensors in functional electrical stimulation. IEEE Trans Rehab Eng. Jun. 1996;4(2):63-72.
Sharma et al., Nonlinear Neuromuscular Electrical Stimulation Tracking Control of a Human Limb. IEEE Trans Neur Sys Rehab Eng. Dec. 2009;17(6):576-84.
Takahashi et al., FES Cycling Chair for the Lower Limbs Disabled People with Electric Motor Power Assist. 9th Annual Conference of the International FES Society. Bournemouth, UK. Sep. 2004. 3 pages.
Willemsen et al., Real-time gait assessment utilizing a new way of accelerometry. J Biomech. 1990;23(8):859-63.
Yeom et al., Autogenic EMG-controlled functional electrical stimulation for ankle dorsiflexion control. J Neurosci Meth. Oct. 30, 2010;193(1):118-25. doi:10.1016/j.jneumeth.2010.08.011. Epub Oct. 30, 2011. 17 pages.
PCT/US2014/071309, Apr. 17, 2015, International Search Report and Written Opinion.
PCT/US2015/034562, Nov. 17, 2015, Invitation to Pay Additional Fees.
PCT/US2015/034562, Feb. 1, 2016, International Search Report and Written Opinion.

* cited by examiner

CLOSED-LOOP HYBRID ORTHOTIC SYSTEM FOR REHABILITATION AND FUNCTIONAL MOBILITY ASSISTANCE

RELATED APPLICATIONS

The present application is a U.S. national stage filing under 35 U.S.C. § 371 based on International Application No. PCT/US2014/071309 entitled "CLOSED-LOOP HYBRID ORTHOTIC SYSTEM FOR REHABILITATION AND FUNCTIONAL MOBILITY ASSISTANCE", filed Dec. 18, 2014, which claims priority under 35 U.S.C. § 119(e) to U.S. Provisional Application Ser. No. 61/917,586 entitled "CLOSED-LOOP HYBRID ORTHOTIC SYSTEM FOR REHABILITATION AND FUNCTIONAL MOBILITY ASSISTANCE", filed Dec. 18, 2013, which is hereby incorporated by reference in its entirety for all purposes.

GOVERNMENT FUNDING

Research leading to various aspects of the present invention was sponsored, at least in part, by the National Science Foundation under Grants No. CMMI-1161260 and CMMI-0547448. The U.S. Government has certain rights in the invention.

FIELD

The present invention generally relates to orthotic devices and, in particular, to hybrid orthotic devices comprising a controller and one or more electrodes.

BACKGROUND

Upper motor neuron lesions (UMNL), which may be caused by neural disorders such as stroke, cerebrovascular accident, spinal cord injury, cerebral palsy, and/or traumatic brain injury, cause disability and paralysis in millions of people. Since the lower motor neuron system and muscles are generally intact in those with UMNL, muscle contractions may be evoked by directly applying electrical stimulus to the muscles via one or more electrodes. This technique, which may be used for rehabilitation and restoration of motor function, may be referred to as neuromuscular electrical stimulation (NMES). It may also be referred to as functional electrical stimulation (FES) when it is applied to produce a functional outcome, such as standing and/or walking.

A number of challenges have been associated with development of NMES devices and methods, including the nonlinear response of muscle to electrical stimulation, load changes during functional movement, unexpected muscle spasticity, time lag between electrical stimulation and muscle force output, uncertainties in muscle physiology (e.g., temperature, pH, and/or architecture), and muscle fatigue. Improved devices and methods for application of electrical stimulation to a human body to produce functional outcomes would be desirable.

SUMMARY

Embodiments described herein generally relate to orthotic devices and, in particular, to hybrid orthotic devices comprising a controller and one or more electrodes. The subject matter of the present invention involves, in some cases, interrelated products, alternative solutions to a particular problem, and/or a plurality of different uses of one or more systems and/or articles.

In some embodiments, an orthotic device is provided. According to certain embodiments, the orthotic device comprises one or more sensors, one or more electrodes, and a nonlinear controller configured to receive input signals from the one or more sensors and deliver output signals to the one or more electrodes.

In another set of embodiments, an orthotic device comprises a bracing element configured to attach to a limb of a person, one or more sensors configured to measure the angle between a first body part of the person and a second body part of the person coupled at a joint, one or more electrodes configured to apply electrical stimulation to one or more body parts of the person, and a nonlinear controller configured to receive input signals from the one or more sensors and deliver output signals to the one or more electrodes.

Methods of providing functional electrical stimulation to a person are also provided. In some embodiments, the method comprises receiving signals from at least one sensor, calculating an amount of electrical stimulation to apply to at least one body part of the person, and delivering electrical stimulation to the at least one body part of the person via at least one electrode.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
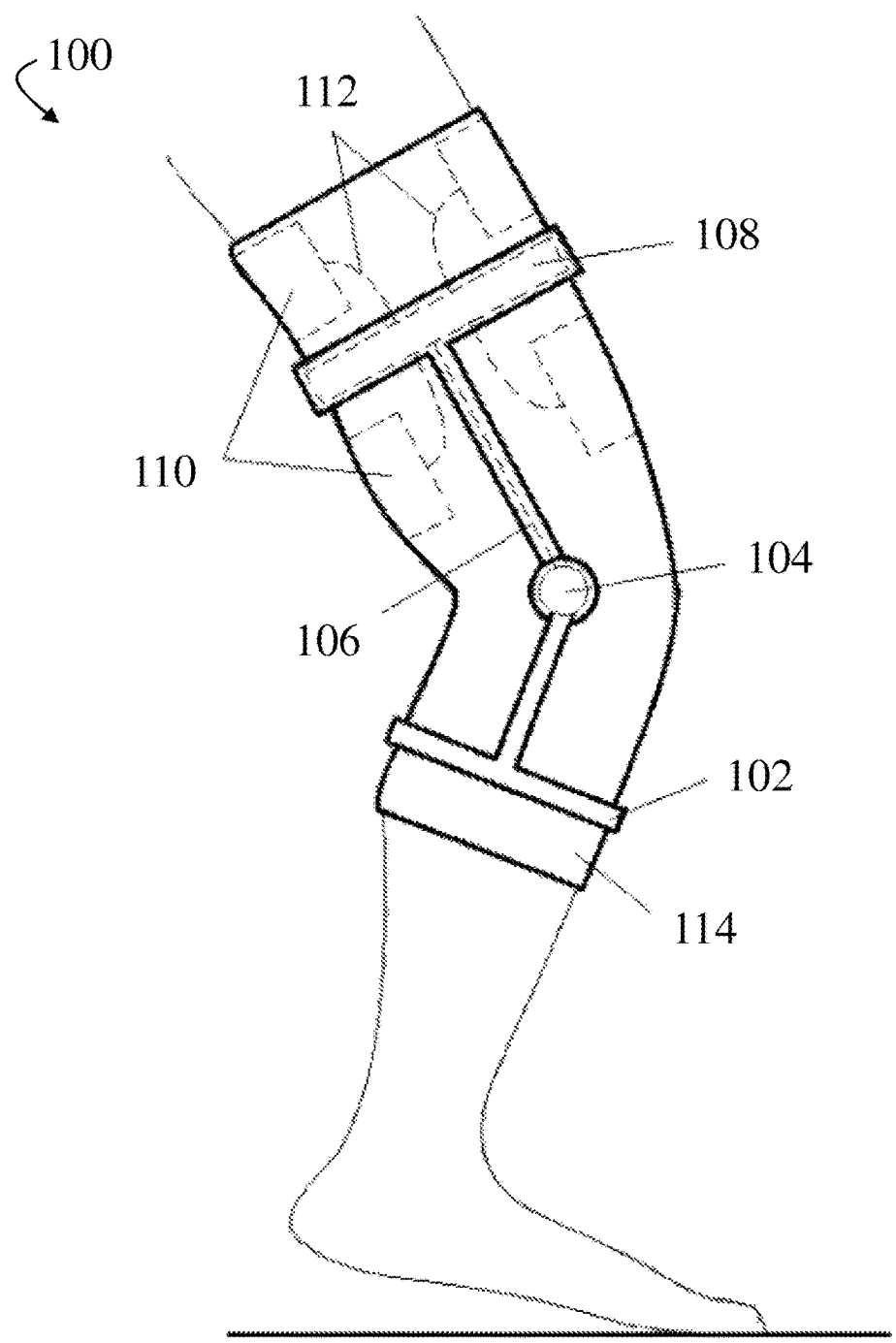
FIG. 1 shows an exemplary schematic illustration of a hybrid orthotic device comprising a knee brace, according to some embodiments.

Hybrid orthotic devices configured to apply electrical stimulation to one or more body parts of a person are generally described. In some embodiments, a hybrid orthotic device comprises one or more sensors, one or more electrodes, and a controller configured to receive input signals from the one or more sensors and deliver output signals to the one or more electrodes. In some embodiments, the controller may be nonlinear in that stimulus signals generated by the controller may be different in different contexts, even for the same inputs to the controller. In certain cases, the nonlinear controller may be configured to store one or more programs, which may, when executed, implement algorithms as described herein. The one or more programs may be associated, in some embodiments, with functional activities (e.g., standing, sitting, and/or walking), and the programs may be configured to enable one or more body parts of a wearer to track a desired trajectory. In some embodiments, a program may implement a Robust Integral of the Sign of the Error (RISE) control method, which will be discussed in more detail below. It may be desirable, in some cases, to implement a RISE-based control method, at least in part because such methods may achieve asymptotic stability, even in the presence of unknown, additive disturbances and parametric uncertainties in a nonlinear system. A RISE-based control method generally does not require knowledge of a muscle model. It may also be desirable to implement a RISE-based control method because such methods may be continuous. In some cases, a program may further implement control methods to compensate for electromechanical delay and/or muscle fatigue. In certain embodiments, a program may further implement adaptive learning methods, such as neural network (NN)-based methods.

In some embodiments, the hybrid orthotic device comprises one or more sensors. In certain cases, at least one of the sensors may be an electrogoniometer. Generally, an electrogoniometer refers to an instrument for measuring angles. In some cases, the electrogoniometer may be attached to the hybrid orthotic device so as to measure the angle between a first body part of a person and a second body part of a person, coupled at a joint, and to which the hybrid orthotic device may be attached. In certain embodiments, at least one of the sensors may be a pressure sensor. In some such embodiments, the pressure sensor may, for example, measure pressure applied by a body part (e.g., a foot) on a surface (e.g., the ground). In some embodiments, at least one of the sensors may be configured to measure velocity of a joint.

The hybrid orthotic device may comprise one or more electrodes. In some embodiments, at least one of the electrodes may be configured to apply electrical stimulation to one or more body parts of a person. For example, at least one of the electrodes may be configured to apply electrical stimulation to the skin of a person and to one or more underlying skeletal muscles. The stimulation may cause the muscles to contract, when above a level, or allow the muscle to relax, when below a level. Non-limiting examples of skeletal muscles and muscle groups that may be stimulated, based on configuration of the hybrid orthotic device, include the quadriceps femoris, hamstrings, triceps surae, tibialis anterior, and biceps femoris. For example, it may be desirable to apply electrical stimulation to portions of the quadriceps femoris muscle group to induce extension of a knee as part of a functional activity, such as standing, sitting, and/or walking. In some embodiments, the electrodes may be bipolar electrodes. In certain cases, the electrodes may be self-adhesive electrodes, and may be rigidly coupled to structural members of the hybrid orthotic device and/or separately attached to a wearer of the device. In some cases, the orthotic device may comprise at least two electrodes.

The hybrid orthotic device may further comprise a controller. In some embodiments, the controller may be a nonlinear controller configured to receive input signals from one or more sensors and deliver output signals to one or more electrodes. The controller may, in certain cases, generate output signals as a nonlinear function of the input signals based at least in part on a determined parameter indicative of muscle fatigue. In some embodiments, the controller may be connected to one or more sensors via electrical leads. In some cases, the electrical leads may comprise power and/or data lines. For example, in certain embodiments, power may be transferred from the controller to the one or more sensors, and data may be transferred from the one or more sensors to the controller. In some embodiments, the controller may be connected to one or more electrodes via electrical leads. In certain cases, the electrical leads may be one-way leads. For example, in some cases, signals may be transferred from the controller to the one or more electrodes, but no data may be transferred from the electrodes to the controller. In some cases, the controller may be connected to at least two electrodes. The controller may be configured to deliver interleaved output signals to the at least two electrodes. In some embodiments, the controller may comprise inputs and outputs for connecting with a computer, for example for programming and/or data logging. The controller may, in some cases, be configured to record data from previous activities.

In some cases, the nonlinear controller may be configured to store one or more programs. The one or more programs may be associated, in some embodiments, with one or more functional activities, and the programs may be configured to enable one or more body parts of the person to track a desired trajectory. In some embodiments, a program may implement a closed-loop control method. A program may, in certain cases, implement a continuous feedback control method. In some cases, a program may implement a control method that yields asymptotic stability for a nonlinear system (e.g., muscle model) in the presence of bounded nonlinear disturbances (e.g., muscle spasticity, electromechanical delays, muscle fatigue). In some embodiments, the program may implement a control method that tracks the time-varying trajectory of at least one body part of the person. The program may, in certain cases, implement a RISE-based control method. In some cases, a program may further implement control methods to compensate for electromechanical delay and/or muscle fatigue. For example, the control method may comprise a predictor-type method to compensate for electromechanical delay. In certain embodiments, a program may further implement adaptive learning methods. For example, a program may implement a control method comprising an adaptive feedforward method. In some embodiments, the adaptive learning methods may comprise neural network (NN)-based methods.

The programs, when executed, may cause the controller to receive and process outputs of one or more sensors and, based on those outputs and/or other data, derive one or more stimulus signals to apply to one or more electrodes. The stimulus signals may have one or more characteristics that change over time, such that the stimulus applied to muscles of a wearer is modulated. In some cases, the program may implement a voltage modulation scheme (e.g., with a fixed frequency and a fixed pulse width) and/or a pulse width modulation scheme (e.g., with a fixed voltage and a fixed frequency). In some cases, the program may implement a frequency modulation scheme (e.g., with a fixed voltage and a fixed pulse width).

One problem that may arise during NMES is rapid onset of muscle fatigue during repeated contractions. The onset of muscle fatigue may be correlated with stimulation parameters such as intensity, frequency, and pattern of stimulation, with higher stimulation frequencies causing muscle to fatigue faster. The controller may be configured to generate stimulus signals based on passage of time and/or indicators of fatigue. In some embodiments, the program may implement a scheme comprising feedback-based frequency modulation to reduce fatigue. In certain cases, the program may implement a modulation scheme that adjusts frequency to maintain body part position tracking error within a specified range. For example, in some cases, the stimulation frequency may be progressively increased or decreased. Starting with a low frequency and changing to a high frequency when muscle output dictates higher demands may more closely mimic biological approaches than constant frequency schemes. In some cases, the program may implement a control method that increases and/or decreases the amplitude and/or frequency of the output signals according to a predefined rule. In certain embodiments, the program may implement a control method that modulates the amplitude and/or frequency of the output signals based at least in part on a value of one or more parameters indicative of muscle fatigue.

The hybrid orthotic device may comprise a bracing element configured to attach to a limb of a person. In some embodiments, the bracing element comprises one or more cuffs. In some embodiments, the bracing element may comprise a first cuff configured to attach to a first body part of a person and a second cuff configured to attach to a second body part of a person, where the first body part and second body part are coupled at a joint (e.g., knee, ankle, elbow, shoulder, wrist, hip). The cuffs may be adjustable and may be tightened or loosened (e.g., such that the cuff fits around a limb, such as a leg). In some cases, the cuffs may be substantially flexible (e.g., resilient), semi-rigid, or substantially rigid (e.g., non-resilient). The cuffs may comprise materials including, but not limited to, fabric (e.g., polyester, nylon, neoprene), plastic, and/or metal (e.g., aluminum). The cuffs may be fastened by any suitable fastener, including those now known in the art. For example, the cuffs may be fastened by one or more Velcro fasteners, buckles, and/or hook fasteners. In some embodiments, the bracing element may further comprise a sleeve. The sleeve may be substantially flexible (e.g., such that it can conform to the limb and/or joint). In certain embodiments, the sleeve may comprise a fabric. The bracing element may, in some cases, allow hinged movement of the joint (e.g., may not inhibit flexion and/or extension of the joint). In some embodiments, the bracing element may advantageously provide lateral and/or rotational stability to the joint. For example, the bracing element may prevent hyperextension and/or excessive rotation of the joint.

In some embodiments, the hybrid orthotic device may further comprise one or more elastic resistance elements. The elastic resistance element may comprise a first end secured to a first location on the bracing element and a second end secured to a second location on the bracing element. In certain cases, the elastic resistance element may comprise a spring and/or an elastic band. It may be desirable, in some cases, for the orthotic device to comprise an elastic resistance element for use in exercising one or more parts of the body.

FIG. 1 shows an exemplary schematic illustration of a hybrid orthotic device, according to some embodiments of the invention. In FIG. 1, hybrid orthotic device 100 comprises bracing element 102, which is configured to be worn on a leg. In some embodiments, the bracing element may comprise one or more cuffs. For example, in FIG. 1, bracing element 102 comprises two cuffs: one that can be positioned around the lower leg, and one that can be positioned around the thigh. In some embodiments, one or more sensors and their associated electrical leads may be embedded in the bracing element. For example, in FIG. 1, sensor 104 and electrical leads 106 are embedded in bracing element 102, with sensor 104 located at a hinge of bracing element 102 located between the two cuffs. Sensor 104 may, in some cases, be an electrogoniometer configured to measure joint angle. Electrical leads 106 may connect sensor 104 to a controller 108, which may also be attached to bracing element 102. The controller may comprise a portable power supply (e.g., batteries) and inputs and outputs for interfacing with sensors, electrodes, and/or external computers. For example, controller 108 may be configured to send power to and receive data (e.g., data about the joint angle) from sensor 104 via electrical leads 106. Controller 108 may also be configured to receive and store programs from and send data to an external computer. Additionally, controller 108 may also be configured to send output stimulation signals to electrodes 110 via electrical leads 112 to cause contractions of the muscles of the wearer to induce a desired joint motion. In some embodiments, leads 112 may be one-way leads (e.g., data may not be transmitted from electrodes 110 to controller 108). In FIG. 1, electrodes 110 and leads 112 are embedded in a sleeve 114. Sleeve 114, which may comprise a flexible material and conform to the joint and leg, may be positioned under bracing element 102. In some embodiments, electrodes 110 may be configured to be in contact with the skin of a person and to transmit electrical stimulation to underlying muscle. In some embodiments, electrodes 110 may be used to activate different muscle groups at the same time.

Figure 2:
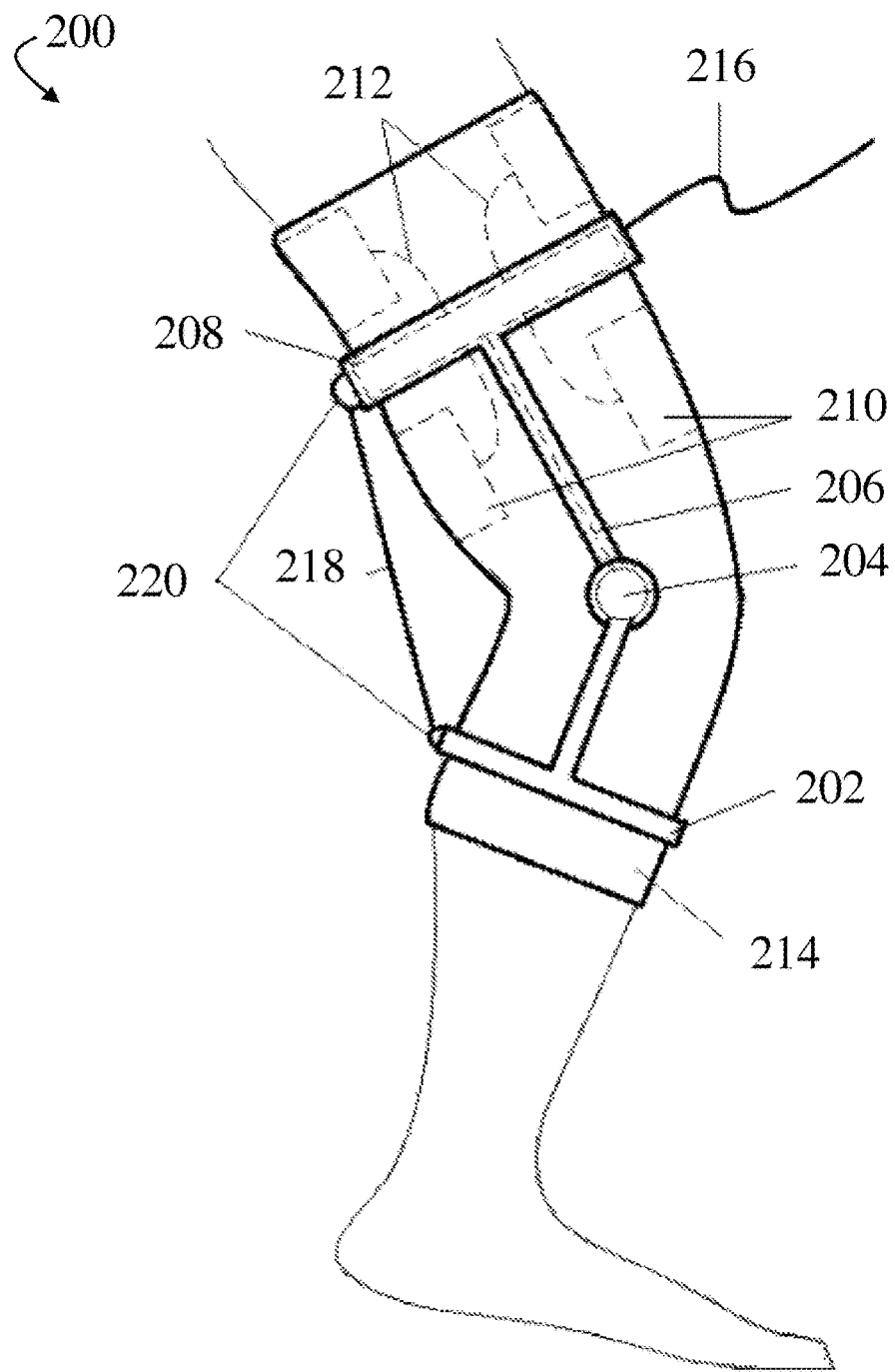
FIG. 2 shows, according to some embodiments, an exemplary schematic illustration of a hybrid orthotic device comprising a knee brace and elastic resistance elements.

An exemplary schematic illustration of a hybrid orthotic device comprising elastic resistance elements is shown in FIG. 2. Like orthotic device 100 in FIG. 1, orthotic device 200 in FIG. 2 comprises a bracing element 202 and a sensor 204, which is connected to controller 208 via electrical leads 206. Sensor 204, electrical leads 206, and controller 208 are embedded in bracing element 202. In FIG. 2, controller 208 is connected to a cable 216. Controller 208 may be configured to receive power from an external power source via cable 216. Controller 208 may also be configured to communicate with an external computer in real time (e.g., for data logging and/or visualization) via cable 216. Additionally, controller 208 is connected to electrodes 210 via electrical leads 212. Electrodes 210 and electrical leads 212 are embedded in a sleeve 214. Orthotic device 200 also comprises elastic resistance element 218, which is attached to bracing element 202 via anchors 220. Elastic resistance element 218 may be a tension or compression element. In some cases, it may be desirable for an orthotic device to comprise one or more elastic resistance elements for exercising a joint. Anchors 220 may allow elastic resistance element 218 to be easily removed and replaced, facilitating exercise that calls for progressive increase and/or decrease of resistance.

Figure 3:
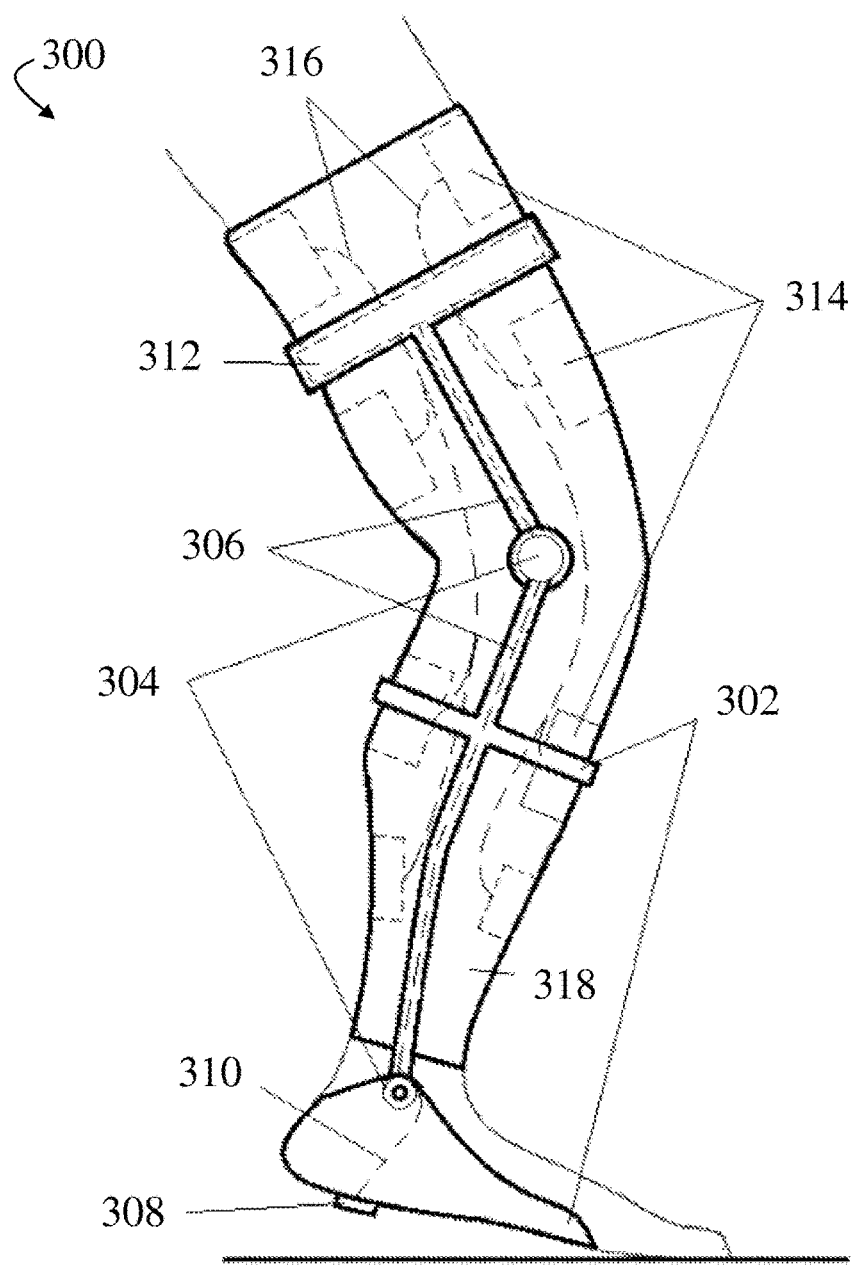
FIG. 3 shows an exemplary schematic illustration of a hybrid orthotic device comprising a knee and ankle brace, according to some embodiments.

FIG. 3 shows an exemplary schematic illustration of a hybrid orthotic device configured to induce movement about the knee and/or ankle joints, according to some embodiments. In FIG. 3, orthotic device 300, which is a knee-ankle-foot orthosis, comprises bracing element 302. Bracing element 302 may comprise one or more hinges and may be substantially flexible, semi-rigid, or rigid. In FIG. 3, bracing element 302 comprises a first adjustable cuff configured to attach to a lower leg and a second adjustable cuff configured to attach to a thigh. Bracing element 302 further comprises a foot piece designed to fit inside a shoe for a foot. A pressure sensor 308 may be in direct contact with the foot piece. Pressure sensor 308 may be configured to collect data relating to contact between the foot and an external surface (e.g., the ground) and to transmit the data to a controller 312 via electrical lead 310. In FIG. 3, additional sensors 304 are embedded in bracing element 302. In some embodiments, at least one of sensors 304 is an electrogoniometer. The electrogoniometer may measure, for example, knee and/or ankle angle. Sensors 304 may be configured to transmit data to controller 312 via electrical leads 306. In some cases, electrical leads 306 and 310 may comprise power and data lines. In FIG. 3, controller 312 is also connected to electrodes 314 via electrical leads 316. Electrodes 314 and electrical leads 316 may be embedded in sleeve 318. In some embodiments, electrodes 314 may be configured to apply stimulation to induce flexion, extension, or rotation of the knee and/or ankle.

Figure 4:
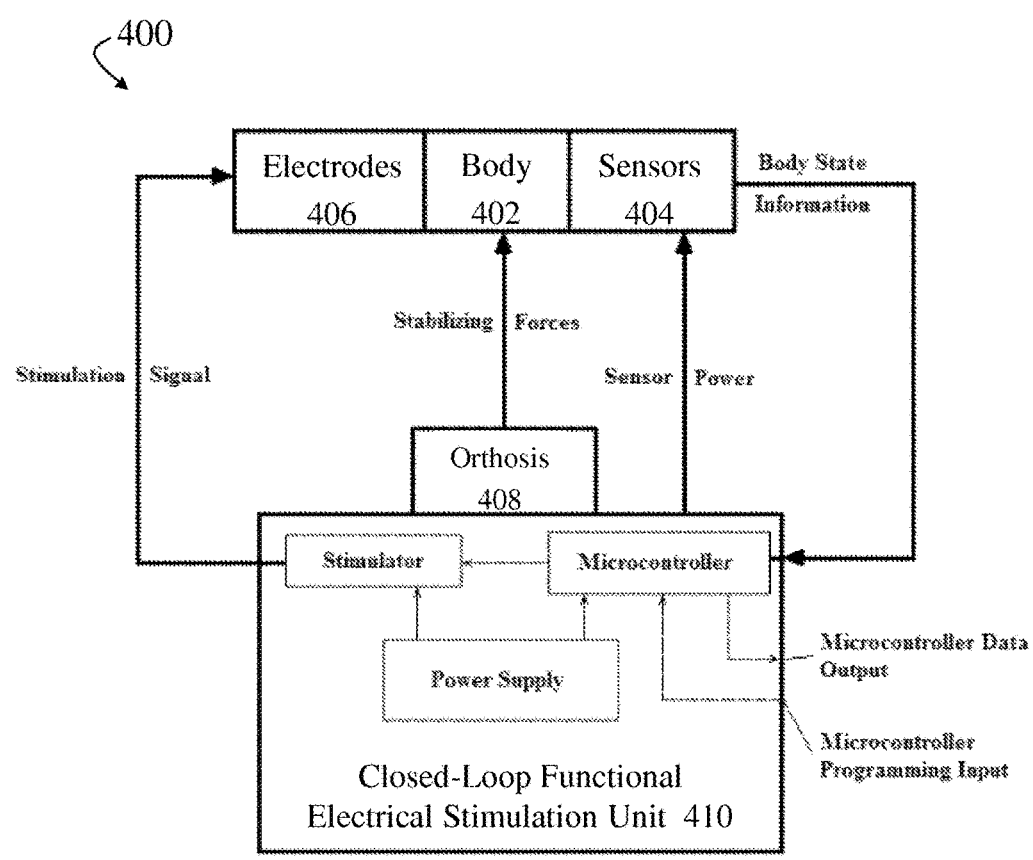
FIG. 4 shows an exemplary block diagram of a system comprising a portable closed-loop functional electrical stimulation unit, according to some embodiments.

FIG. 4 displays an exemplary schematic block diagram illustrating the interactions between components of a system comprising a hybrid orthotic device, according to some embodiments. It should be appreciated that FIG. 4 is a functional block diagram and the components represented in that block diagram may be configured and positioned in any suitable way, including as illustrated in any of FIGS. 1-3. In FIG. 4, system 400 comprises a body 402, sensors 404, electrodes 406, orthosis 408, and a closed-loop functional electrical stimulation (CL-FES) unit 410. Sensors 404 are in direct contact with body 402, and they transmit body state information to CL-FES unit 410. CL-FES unit 410 comprises a microcontroller, a stimulator, and a power supply. The power supply may supply power to the microcontroller and the stimulator, and may additionally supply power to sensors 404. The microcontroller receives body state information from sensors 404. Additionally, the microcontroller is configured to receive programming input from an external computer and to transmit data to the external computer. In some embodiments, a connection to an external computer may be active while the device is in operation to enable the external computer to perform some or all of the control functions. The microcontroller can also send information to the stimulator, which transmits a stimulation signal to electrodes 406. Electrodes 406 are in direct contact with body 402, and the electrical stimulation may induce movement of body 402 such that a functional activity may be performed. CL-FES unit 410 is also in direct contact with an orthosis 408, which may provide stabilizing forces to body 402.

Figure 5:
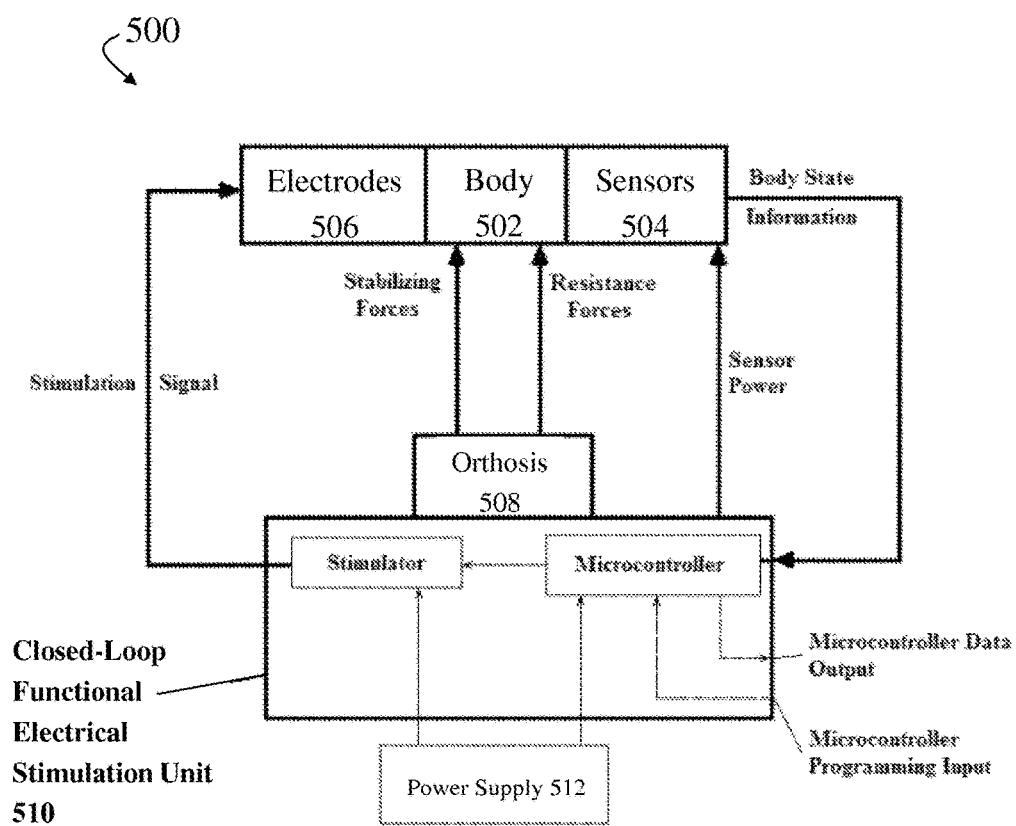
FIG. 5 shows, according to some embodiments, an exemplary block diagram of a system comprising an externally-powered closed-loop functional electrical stimulation unit.

An exemplary schematic block diagram illustrating the interactions between components of a system comprising an externally-powered hybrid orthotic device, according to some embodiments, is shown in FIG. 5. In FIG. 5, CL-FES unit 510 comprises a stimulator and microcontroller, like CL-FES unit 410. However, unlike CL-FES unit 410, CL-FES unit 510 does not comprise a power source. Rather, power is supplied from external power supply 512. Additionally, in FIG. 5, CL-FES unit 510 is in direct contact with orthosis 508, which comprises one or more elastic resistance units. Orthosis 508 is therefore configured to provide not only stabilizing forces but also resistance forces to body 502.

Figure 6:
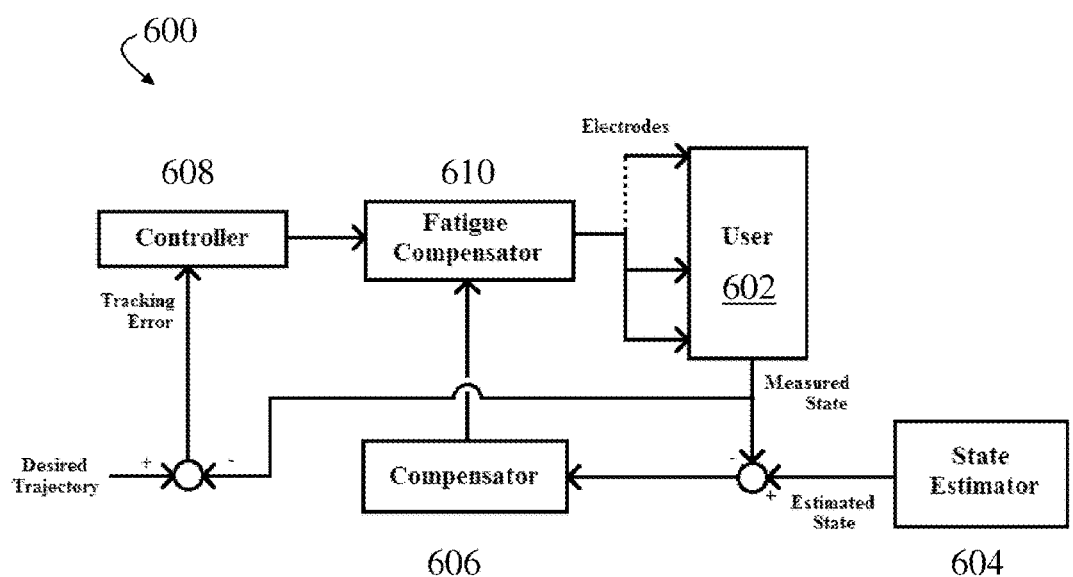
FIG. 6 shows an exemplary block diagram of a system comprising a controller for an orthotic device, according to some embodiments.

FIG. 6 displays an exemplary schematic block diagram illustrating the interactions between components of a controller, according to some embodiments. In FIG. 6, a state of user 602 is measured. The state may be represented in whole or in part by sensor outputs and may include, for example, joint angle. The measured state may then be compared to the state estimated by state estimator 604. The difference between the measured state and the estimated state may be sent to compensator 606, which utilizes a compensating method to compensate for differences between the measured and estimated states. The measured state may also be compared to the desired trajectory, and the tracking error may be sent to controller 608. Controller 608 utilizes a control method to minimize the tracking error and calculate the amplitude, frequency, and pulse width of output signals (which may serve as stimulus signals input to electrodes) to enable user 602 to most closely follow the desired trajectory. Output from compensator 606 and controller 608 may be sent to fatigue compensator 610, which compensates for muscle fatigue induced by electrical stimulation. Compensation, for example, may increase stimulation as increased fatigue is measured. The output signals may then be sent to electrodes to apply electrical stimulation to user 602.

Some embodiments relate to methods of providing functional electrical stimulation to a person. For example, a method may comprise the step of receiving signals from at least one sensor. Additionally, the method may comprise the steps of calculating an amount of electrical stimulation to apply to at least one body part of the person and delivering electrical stimulation to the at least one body part of the person.

Joint Model

It may be desirable, in some cases, to model the total dynamics of a joint to facilitate development of a controller that could enable movement about the joint to follow a desired trajectory. In some embodiments, the total dynamics of a joint can be modeled as:

$$M_I + M_e + M_g + M_v + \tau_d = \tau \quad (1)$$

where $M_I$ represents inertial effects of one or more body parts about the joint, $M_e$ represents elastic effects due to joint stiffness, $M_g$ represents gravitational effects, $M_v$ represents viscous effects due to damping in the musculotendon complex, $\tau_d$ represents one or more unknown bounded disturbances (e.g., muscle spasticity, dynamic fatigue, signal and response delays, changing muscle geometry, and/or load changes during functional tasks), and $\tau$ represents the torque produced at the joint. The first and second time derivatives of unknown disturbance $\tau_d$ can be assumed to exist and to be bounded.

Inertial effects $M_I$ can be modeled, in some cases, as:

$$M_I(\ddot{q}(t)) = J\ddot{q}(t) \quad (2)$$

where $\ddot{q}(t)$ denotes the angular acceleration of the one or more body parts about the joint, and $J$ denotes the unknown inertia of the one or more body parts.

In certain cases, elastic effects $M_e$ can be modeled as:

$$M_e(q(t)) = -k_1 e^{-k_2 q(t)}(q(t) - k_3) \quad (3)$$

where $q(t)$ denotes the angular position of the one or more body parts about the joint, and $k_1$, $k_2$, and $k_3$ are unknown positive coefficients.

Gravitational effects $M_g$ may be modeled as:

$$M_g(q(t)) = -mgl \sin(q(t)) \qquad (4)$$

where m denotes the unknown combined mass of the body parts, l is the unknown distance between the joint and the center of mass of the body parts, and g denotes the gravitational acceleration. Gravitational acceleration generally refers to the value of about 9.8 meters per second squared (m/s$^2$).

Viscous effects $M_v$ may be modeled as:

$$M_v(\dot{q}(t)) = B_1 \tan h(-B_2 \dot{q}(t)) - B_3 \dot{q}(t) \qquad (5)$$

where $\dot{q}(t)$ denotes the angular velocity of the body parts about the joint and $B_1$, $B_2$, and $B_3$ are unknown positive constants.

Torque $\tau(t)$ about the joint may be produced through muscle tendon forces $F_T(t)$, such as those generated through electrical stimulation of one or more muscles. Torque $\tau(t)$ may be related to musculotendon force $F_T(t)$ through the relation:

$$\tau(t) = \zeta(q(t)) F_T(t) \qquad (6)$$

where $\zeta(q(t))$ represents a positive moment arm that changes with extension and movement of the body parts. The moment arm may have unique values for a given range of motion. The unique values may be considered continuously differentiable, positive, monotonic, and bounded. The unique values may also be considered to have a bounded first time derivative. The total musculotendon force may be a net sum of active forces generated by contractile, elastic, and viscous elements. The forces may have dynamic characteristics. For example, in some cases, a passive elastic element may increase with increasing muscle length. In some cases, the musculotendon force generated at the tendon may be the projection of the net sum of the elements along the line parallel to the tendon.

In some cases, the torque at the joint may be delayed. In some such cases, torque $\tau(t)$ may be represented by $u(t-t_\tau)$, where $t_\tau$ represents the electromechanical delay. The relation between the torque and musculotendon force may then be written as:

$$u(t-t_\tau) = \zeta(q(t)) F_T(t-t_\tau) \qquad (7)$$

In certain cases, the musculotendon force $F_T(t)$ may be modeled as:

$$F_T = F \cos \alpha(q(t)) \qquad (8)$$

where $\alpha(q(t))$ is the pennation angle between the tendon and the muscle. For example, for the human quadriceps muscle, the pennation angle may change monotonically during contraction and may be a continuously differentiable, positive, monotonic, and bounded function with a bounded first time derivative.

In some embodiments, there may be asynchronous electrical stimulation of one or more muscles. In some such cases, there may be N stimulation channels in the system. Since each channel can activate different sets of muscle units, the corresponding dynamics may be different depending on the switching signal. For example, the dynamics may be modeled as:

$$M_I + M_e + M_g + M_v + \tau_d = \tau_i + \tau_i + \tau_j + \ldots + \tau_N \qquad (9)$$

where $\tau_i$ and $\tau_j$ represent the torque produced by stimulation of the i$^{th}$ and j$^{th}$ subsystems, respectively. The torque produced by stimulation of the i$^{th}$ subsystem may be related to the musculotendon force as:

$$\tau_i(t) = \zeta_i(q(t)) F_{T,i}(t) \qquad (10)$$

where musculotendon force $F_{T,i} = F_i \cos \alpha_i(q)$ and $F_i$ is the force produced by the recruited muscle in the i$^{th}$ subsystem.

In some embodiments, the relationship between musculotendon force $F_T$ and the applied stimulation V(t) can be expressed as:

$$F_T(t) = \eta(t) V(t) \qquad (11)$$

where $\eta(t)$ is an unknown nonlinear function that is continuously differentiable, nonzero, positive, monotonic, and bounded, with a bounded first time derivative. In this example, V(t) may represent a voltage. However, the specific form in which the stimulus is applied is not critical to the invention, and the stimulus may be applied alternatively or additionally as a current or in any other suitable form. It may, in some cases, be desirable to introduce unknown nonlinear function $\eta(t)$, since it may enable the muscle contraction to be considered under general dynamic conditions in the subsequent control development. The unknown, uncertain function $\eta(t)$ can capture the dynamic characteristics of muscle recruitment, muscle force-length, and muscle force-velocity relationships, as well as active and passive characteristics. If electromechanical delay is taken into account, the relation may be written as:

$$F_T(t-t_\tau) = \eta(q(t), \dot{q}(t)) V(t-t_\tau) \qquad (12)$$

to capture the latency present between the application of stimulation and production of force.

Control Development

In some embodiments, a controller may enable one or more body parts coupled at a joint to track a desired trajectory $q_d(t)$, where $q_d(t)$ and its i$^{th}$ derivatives $q_d^i(t)$ are bounded and within the range of motion of the joint for i=1, 2, 3, and 4. In some cases, desired trajectory $q_d(t)$ may be based on joint kinetics and/or joint kinematics. In some embodiments, desired trajectory $q_d(t)$ may be based on body part position. Alternatively, the desired trajectory may comprise continuous signals, periodic signals, step functions, and/or sinusoidal functions. In some cases, the periodic signals may have different frequencies and/or the step functions may have changes in the dynamic load.

In some embodiments, a position tracking error may be defined as:

$$e_1(t) = q_d(t) - q(t) \qquad (13)$$

Two filtered tracking errors $e_2(t)$ and r(t) may be introduced to facilitate closed-loop error system development and stability analysis. Filtered tracking error $e_2(t)$ may be expressed as:

$$e_2(t) \triangleq \dot{e}_1(t) + \alpha_1 e_1(t) \qquad (14)$$

where $\alpha_1$ is a positive constant control gain.

Filtered tracking error r(t) may be expressed as:

$$r(t) \triangleq \dot{e}_2(t) + \alpha_2 e_2(t) \qquad (15)$$

where $\alpha_2$ is a positive constant control gain. In some cases, filtered tracking error r(t) may not be used in the controller due to a dependence on angular acceleration measurements.

Multiplying Equation 15 by J and using the above expressions, the following expression can be obtained:

$$Jr = W - \Omega V + \tau_d \qquad (16)$$

where auxiliary signal W is defined as:

$$W = J(\ddot{q}_d + \alpha_1 \dot{e}_1 + \alpha_2 e_2) + M_e + M_g + M_v \qquad (17)$$

and auxiliary function $\Omega$ is defined as:

$$\Omega(q,t) = \zeta(q(t)) \eta(t) \cos \alpha(q(t)) \qquad (18)$$

Multiplying Equation 16 by $\Omega^{-1}$, the following expression can be obtained:

$$J_\Omega r = W_\Omega - V + \tau_{d\Omega} \qquad (19)$$

where $J_\Omega = \Omega^{-1}J$, $W_\Omega = \Omega^{-1}W = J_\Omega(\ddot{q}_d + \alpha_1\dot{e}_1 + \alpha_2 e_2) + \Omega^{-1}(M_e + M_g + M_v)$, and $\tau_{d\Omega} = \Omega^{-1}\tau_d$.

In some cases, the following open-loop error system for Equation 19 may be obtained:

$$J_\Omega \dot{r} = -\frac{1}{2}\dot{J}_\Omega r + N - \dot{V} - e_2 \qquad (20)$$

where N denotes the unmeasureable auxiliary term:

$$N = \dot{W}_\Omega + e_2 - \frac{1}{2}\dot{J}_\Omega r + \tau_{d\Omega}(q, t) \qquad (21)$$

In some embodiments, it may be desirable to obtain the above expressions for Equations 20 and 21 to facilitate stability analysis. Another unmeasureable auxiliary term $N_d$ may be defined as:

$$N_d = \dot{J}_\Omega(q_d)\ddot{q}_d + J_\Omega(q_d)\dddot{q}_d +$$
$$\dot{M}_{e\Omega}(q_d) + \dot{M}_{g\Omega}(q_d) + \dot{M}_{v\Omega}(q_d) + \tau_{d\Omega}(q_d, \tau) \qquad (22)$$

where $$M_{e\Omega} = \frac{M_e}{\Omega},$$

$$M_{g\Omega} = \frac{M_g}{\Omega},$$

and $$M_{v\Omega} = \frac{M_v}{\Omega}.$$

The open-loop error system can then be expressed as:

$$J_\Omega \dot{r} = -\dot{V} - e_2 + \tilde{N} + N_d - \frac{1}{2}\dot{J}_\Omega r \qquad (23)$$

where unmeasureable auxiliary term $\tilde{N}(t)$ is defined as $\tilde{N}(t) = N - N_d$. In some cases, it may be desirable to express the open-loop error system as in Equation 23 to segregate the uncertain nonlinearities and disturbances from the model into terms that are bounded by state-dependent bounds and terms that are upper bounded by constants. For example, in certain cases, the mean value theorem may be applied to upper bound unmeasureable auxiliary term $\tilde{N}(t)$ by state-dependent terms as:

$$\|\tilde{N}\| \leq \rho(\|z\|)\|z\| \qquad (24)$$

where $z(t) \triangleq [e_1^T \ e_2^T \ r^T]^T$ and $\rho(\|z\|)$ is a positive, globally invertible, nondecreasing function. In some cases, the fact that $q_d(t)$, $q_d^i(t) \in L_\infty$ = i=1, 2, 3, 4 can be used to upper bound $N_d$ as:

$$\|N_d\| \leq \zeta_{N_d}, \|\dot{N}_d\| \leq \zeta_{\dot{N}_d} \qquad (25)$$

where $\zeta_{N_d}$ and $\zeta_{\dot{N}_d}$ are known positive constants.

Based on the joint dynamics, the control input V(t) may be designed as:

$$V(t) \triangleq (k_s+1)e_2(t) - (k_s+1)e_2(0) + \int_0^t [(k_s+1)\alpha_2 e_2(\tau) + \beta sgn(e_2(\tau))]d\tau \qquad (26)$$

where $k_s$ and $\beta$ are positive constant adjustable control gains, and sgn denotes the signum function. In some cases, the time derivative of Equation 26 looks like a discontinuous sliding mode controller. Sliding mode control may be desirable because it is a method that can be used to reject the additive bounded disturbances present in the muscle dynamics (e.g., muscle spasticity, load changes, electromechanical delays) while still obtaining an asymptotic stability result. In some cases, the controller in Equation 26 can be implemented as a continuous controller (i.e., the unique integral of the sign of the error) while still yielding an asymptotic stability result. A controller using the input of Equation 26 may be referred to as a robust integral of the sign of the error (RISE) based controller. Equation 26 can ensure that all system signals are bounded under closed-loop operation. The position tracking error may be regulated in the sense that:

$$\|e_1(t)\| \to 0 \text{ as } t \to 0 \qquad (27)$$

The controller may yield semi-global asymptotic tracking provided the control gain $k_s$ is selected sufficiently large and $\beta$ is selected according to the sufficient condition:

$$\beta > \left(\zeta_{N_d} + \frac{1}{\alpha_2}\zeta_{\dot{N}_d}\right) \qquad (28)$$

The asymptotic stability can be seen in the following Lyapunov-based proof. In some cases, D is a domain in $R^{3+1}$ containing $y(t)=0$, where $y(t)$ is defined as:

$$y(t) \triangleq [z^T \sqrt{P(t)}]^T \qquad (29)$$

and auxiliary function P(t) is defined as:

$$P(t) \triangleq \beta\|e_2(0)\| - e_2(0)^T N_d(0) - \int_0^t L(\tau)d\tau. \qquad (30)$$

The auxiliary function L(t) can be defined as:

$$L(t) \triangleq r^T(N_d(t) - \beta sgn(e_2)). \qquad (31)$$

The derivative of P(t) can be expressed as:

$$\dot{P}(t) = -L(t) \triangleq -r^T(N_d(t) - \beta sgn(e_2)). \qquad (32)$$

The following inequality can then be obtained:

$$\int_0^t L(\tau)d\tau \leq \beta\|e_2(0)\| - e_2(0)^T N_d(0). \qquad (33)$$

Equation 33 can be used to conclude that $P(t) \geq 0$.

In certain cases, $V_L(y,t)$ can be a continuously differentiable, positive definite function defined as:

$$V_L(y, t) \triangleq e_1^T e_1 + \frac{1}{2}e_2^T e_2 + \frac{1}{2}r^T J_\Omega r + P \qquad (34)$$

that satisfies the inequalities:

$$U_1(y) \leq V_L(y,t) \leq U_2(y) \qquad (35)$$

where $U_1$ and $U_2$ are continuous, positive definite functions. The derivative of $V_L$ can be expressed as:

$$\dot{V}_L(y,t) = -(2\alpha_1 - 1)e_1^T e_1 - (\alpha_2 - 1)e_2^T e_2 - r^T r + r^T \tilde{N} - k_s r^T r. \qquad (36)$$

The unique integral signum term in the RISE controller can be used to compensate for the disturbance terms included in $N_d$, provided the control gain $\beta$ is selected according to Equation 28. The term $r^T(t)\tilde{N}(e_1, e_2, r, t)$ can be upper bounded by:

$$\|r\tilde{N}\| \leq \rho(\|z\|)\|z\|\|r\| \qquad (37)$$

to obtain:

$$\dot{V}_L(y,t) \leq -\min\{2\alpha_1 - 1, \alpha_2 - 1, 1\}\|z\|^2 + [\rho(\|z\|)\|z\|\|r\| - k_s\|r\|^2]. \qquad (38)$$

Completing the squares for the bracketed terms yields:

$$\dot{V}_L(y, t) \leq -\min\{2\alpha_1 - 1, \alpha_2 - 1, 1\}\|z\|^2 + \frac{\rho^2(\|z\|)\|z\|^2}{4k_s}. \quad (39)$$

The following expression can be obtained from Equation 39:

$$\dot{V}_L(y,t) \leq -U(y) \quad (40)$$

where $U(y)$ is a continuous positive definite function, provided $k_s$ is selected sufficiently large based on the initial conditions of the system. The region of attraction can be made arbitrarily large to include any initial conditions by increasing the control gain $k_s$ (i.e., a semi-global type of stability result). Semi-global asymptotic tracking can therefore be achieved.

RISE+EMD Delay

In some embodiments, a controller may be configured to store a plurality of programs. A program may be selected and executed based on a determined user activity. In some embodiments a program may be selected based on direct user input. In other embodiments, the program may be selected based on sensing user behavior or from other context information. Some or all of the programs may implement an algorithm compensating for electromechanical delay (EMD) during neuromuscular electrical stimulation. EMD generally refers to a biological artifact that arises due to a time lag between application of electrical stimulation and tension development in a muscle, and it may cause degraded performance and instability during neuromuscular electrical stimulation. Without wishing to be bound by any particular theory, EMD may be caused at least in part by the finite propagation time of chemical ions in muscle, cross-bridge formation between actin-myosin filaments, stretching of the series elastic components in response to the external electrical input, and/or synaptic transmission delays. In some cases, EMD may vary with the input signal frequency.

In some cases, the algorithm may comprise a predictive term that actively accounts for EMD. In certain cases, filtered error signal $e_2(t)$ may be expressed as:

$$e_2 = \dot{e}_1 + \alpha e_1 - B\int_{t-t_\tau}^{t} V(\theta)d\theta \quad (41)$$

where $\alpha$ and $B$ are known control gain constants. Auxiliary function $\Omega$ may be defined as:

$$\Omega(q,t) = \zeta(q(t))\eta(t) \quad (42)$$

where $\zeta(q(t))$ represents a positive moment arm and $\eta(t)$ represents an unknown nonlinear function. The error $\xi$ between $B$ and $J_\Omega^{-1}$ may be defined by:

$$\xi = B - \frac{\Omega}{J} \quad (43)$$

where $\xi$ satisfies the relation $|\xi| \leq \bar{\xi}$ and $\bar{\xi}$ is a known constant.

In some embodiments, the open-loop tracking error system may be developed by multiplying $J_\Omega$ by the time derivative of $e_2$ to obtain:

$$J_\Omega \dot{e}_2 = \quad (44)$$

$$J_\Omega \ddot{q}_d + M_{e\Omega} + M_{g\Omega} + M_{v\Omega} + \tau_{d\Omega} + \alpha J_\Omega \dot{e}_1 - V - J_\Omega \xi[V - V_\tau]$$

where $$M_{e\Omega} = \frac{M_e}{\Omega},$$

$$M_{g\Omega} = \frac{M_g}{\Omega},$$

and $$M_{v\Omega} = \frac{M_v}{\Omega}.$$

In some such embodiments, auxiliary term $N_d$ can be defined as:

$$N_d = J_{\Omega d}\ddot{q}_d + M_{v\Omega d} + M_{g\Omega d} + M_{e\Omega d} \quad (45)$$

where the notation $J_{\Omega d}$, $M_{e\Omega d}$, $M_{g\Omega d}$, and $M_{v\Omega d}$ represent $J_\Omega$, $M_{e\Omega}$, $M_{g\Omega}$, and $M_{v\Omega}$ expressed in terms of desired limb position and velocity.

In some embodiments, control input $V(t)$ may be expressed as:

$$V = k_b e_2 \quad (46)$$

where $k_b$ is a known control gain that can be expanded as $k_b = k_{b_1} + k_{b_2} + k_{b_3}$, and $k_{b_1}$, $k_{b_2}$, and $k_{b_3}$ are known constants.

In certain cases, the closed-loop error system can be determined by adding and subtracting auxiliary term $N_d$ to $J_\Omega \dot{e}_2$ and using other relations to arrive at:

$$J_\Omega \dot{e}_2 = -\frac{1}{2}\dot{J}_\Omega e_2 + \tilde{N} + S - e_1 - k_b e_2 - k_b J_\Omega \xi[e_2 - e_{2\tau}] \quad (47)$$

where the auxiliary terms $\tilde{N}$, $N$, and $S$ are defined as:

$$N = \frac{1}{2}\dot{J}_\Omega e_2 + J_\Omega \ddot{q}_d + M_{e\Omega} + M_{g\Omega} + \quad (48)$$

$$M_{v\Omega} + \alpha J_\Omega e_2 - \alpha^2 J_\Omega e_1 + e_1 + \alpha J_\Omega B \int_{t-t_\tau}^{t} V(\theta) d\theta$$

$$\tilde{N} = N - N_d \quad (49)$$

$$S = N_d + d_\Omega \quad (50)$$

where $\tilde{N}$ can be upper bounded as:

$$\tilde{N} \leq \rho(\|z\|)\|z\| \quad (51)$$

where $\rho(\|z\|)$ is a positive, globally invertible, nondecreasing function and z is defined as $z = [e_1 \; e_2 \; e_z]^T$, where $e_z$ is defined as:

$$e_z = \int_{t-\tau}^{t} V(\theta) d\theta \quad (52)$$

S can be upper bounded as:

$$\|S\| \leq \in \quad (53)$$

where $\in$ is a known constant.

Lyapunov-Karsovskii functionals P and Q can be defined as:

$$P = \omega \int_{t-t_\tau}^{t} \left( \int_{s}^{t} V(\theta)^2 d\theta \right) ds \quad (54)$$

$$Q = \frac{\bar{\xi} J_2 k_b}{2} \int_{t-t_\tau}^{t} e_2(\theta)^2 d\theta \quad (55)$$

where $\omega$ is a known constant.

The controller given in Equation 46 can ensure semi-global uniformly ultimately bounded tracking:

$$|e_1(t)| \leq \in_0 \exp(-\in_1 t) + \in_2 \quad (56)$$

where $\in_0$, $\in_1$, and $\in_2$ are constants, provided control gains $\alpha$ and $k_b$ are selected according to sufficient conditions:

$$\alpha > \frac{B^2\tau}{2\omega}, k_{b_3} > \frac{2\bar{\xi}J_2(k_{b_1}+k_{b_2})+\omega k_b^2\tau}{1-2\bar{\xi}J_2} \quad (57)$$

The sufficient condition for $k_{b_3}$ can be satisfied by selecting $\omega$, $k_{b_1}$, and $k_{b_2}$ sufficiently small and $k_{b_3}$ sufficiently large, provided $1-2\bar{\xi}J_2>0$.

RISE+Neural Network

In some embodiments, the controller comprises a neural network (NN) based feed forward controller that is augmented with a continuous robust feedback term to yield an asymptotic result despite an uncertain, nonlinear muscle response. Such a controller may be implemented as part of a program or in any other suitable way. In some cases, it may be desirable to use NN-based controllers with an adaptive element that can adjust to unstructured, nonlinear disturbances in the muscle model. Use of NN-based controllers may, in some cases, reduce the tracking error for a given stimulation input. The ability of neural networks to learn uncertain and unknown muscle dynamics may be complemented by the ability of RISE to compensate for additive system disturbances and NN approximation error.

In some cases, the open-loop tracking error system may be developed by multiplying the expression for filtered tracking error r(t) in Equation 15 by $J/\Omega$ to obtain:

$$J_\Omega r = J_\Omega(\alpha_2 e_2 + \alpha_1 \dot{e}_1 + \ddot{q}_d) + M_{e\Omega} + M_{g\Omega} + M_{v\Omega} - V + \tau_{d\Omega} \quad (58)$$

Equation 58 may be rewritten as:

$$J_\Omega r = f_d + S - V + \tau_{d\Omega} \quad (59)$$

where $f_d$ may be defined as:

$$f_d = M_{e\Omega d} + M_{g\Omega d} + M_{v\Omega d} + J_{\Omega d}\ddot{q}_d \quad (60)$$

and S may be defined as:

$$S = J_\Omega(\alpha_2 e_2 + \alpha_1 \dot{e}_1) + J_\Omega \ddot{q}_d - J_{\Omega d}\ddot{q}_d + M_{e\Omega} + M_{g\Omega} + M_{v\Omega} - (M_{e\Omega d} + M_{g\Omega d} + M_{v\Omega d}) \quad (61)$$

In some embodiments, S may be a compact, simply connected set of $R^4$, and C(S) may be defined as the space where $f_d$ is continuous. In some such embodiments, there exist weights and thresholds such that the function $f_d$ may be represented by a three-layer neural network as:

$$f_d = W^T\sigma(U^T x_d) + \in(x_d) \quad (62)$$

where $x_d(t)=[1\ q_d(t)\ \dot{q}_d(t)\ \ddot{q}_d(t)]^T$. $U \in R^{4\times N_1}$ and $W \in R^{N_1+1}$ are bounded constant ideal weight matrices for the first-to-second and second-to-third layers, respectively, where $N_1$ is the number of neurons in the hidden layer. $\sigma$ is the sigmoid activation function $\sigma(\cdot): R^4 \to R^{N_1+1}$, and $\in(x_d)$ is the functional reconstruction error. In some cases, the additional term "1" in the input vector $x_d$ and activation term $\sigma$ may allow for thresholds to be included as the first columns of the weight matrices, such that any estimation of W and U includes estimation of the thresholds. In some cases, a three-layer NN approximation for $f_d$ may be given as:

$$\hat{f}_d = \hat{W}^T\sigma(\hat{U}^T x_d) \quad (63)$$

where $\hat{W}(t)$ and $\hat{U}(t)$ are estimates of the ideal weight matrices. The estimate mismatches may be defined as $\tilde{U}=U-\hat{U}$ and $\tilde{W}=W-\hat{W}$. The mismatch for the hidden-layer output error may be defined as:

$$\tilde{\sigma}=\sigma-\hat{\sigma}=\sigma(U^T x_d)-\sigma(\hat{U}^T x_d) \quad (64)$$

The ideal weights may be assumed to exist and to be bounded by positive values such that:

$$\|U\|_F^2 = tr(U^T U) = vec(U)^T vec(U) \le \bar{U}_B \quad (65)$$

$$\|W\|_F^2 = tr(W^T W) = vec(W)^T vec(W) \le \bar{W}_B \quad (66)$$

where $\|\cdot\|_F$ is the Frobenius norm of a matrix and tr($\cdot$) is the trace of a matrix.

Based on the assumption that the desired trajectory is bounded, the following inequalities may hold:

$$|\in(x_d)| \le \in_{b_1}, |\in(\dot{x}_d)| \le \in_{b_2}, |\in(\ddot{x}_d)| \le \in_{b_3} \quad (67)$$

where $\in_{b_1}$, $\in_{b_2}$, and $\in_{b_3}$ are known positive constants.

In some embodiments, a closed-loop error system may be developed. In some cases, the NN structure may be developed in terms of the desired trajectories. This may be desirable, in certain cases, in order to avoid the use of acceleration measurements. In some cases, strategic separation and regrouping of terms may be needed to overcome the challenge that while the NN estimates may be upper bounded by constants, the time derivatives of the terms may be state-dependent.

In some cases, the control input may be:

$$V = \hat{f}_d + \mu \quad (68)$$

where $\mu$ is the RISE feedback term defined as:

$$\mu \triangleq (k_s+1)e_2(t) - (k_s+1)e_2(0) + \nu \quad (69)$$

where $k_s$ is a positive constant adjustable control gain and v(t) is the generalized solution to:

$$\dot{\nu} = (k_s+1)\alpha_2 e_2(t) + \beta_1 sgn(e_2(t)), \nu(0)=0 \quad (70)$$

where $\beta_1$ is a positive constant adjustable control gain. The estimates for the NN weights may be generated using a projection algorithm as:

$$\dot{\hat{W}} = proj(\Gamma_1 \hat{\sigma}' \hat{U}^T \dot{x}_d e_2^T) \quad (71)$$

$$\dot{\hat{U}} = proj(\Gamma_2 \dot{x}_d (\hat{\sigma}'^T \hat{W} e_2)^T) \quad (72)$$

where $\Gamma_1$ and $\Gamma_2$ are constant, positive definite, symmetric gain matrices. It should be noted that the expressions for estimated NN weights may vary depending on the desired tasks and other characteristics of the controller.

The NN-based feedforward component $\hat{f}_d$ may be used to approximate the desired musculoskeletal dynamics $f_d$. The NN component may approximate the desired function through adaptive weight estimates that are adjusted online via the adaptive law given in Equations 71 and 72. In some cases, the RISE feedback controller $\mu(t)$ has implicit learning characteristics that maintain the robustness of the system in the presence of additive disturbances and residual function approximation error. One role of the RISE feedback controller may be to keep the system stable while the NN approximates the system dynamics.

The closed-loop tracking error system may be developed by substituting Equation 68 into Equation 59 as:

$$J_\Omega r = \tilde{f}_d + S - \mu + \tau_{d\Omega} \quad (73)$$

where $\tilde{f}_d = f_d - \hat{f}_d$.

To facilitate subsequent closed-loop stability analysis, the time derivative of Equation 73 may be determined as:

$$J_\Omega \dot{r} = -\dot{J}_\Omega r + [/\$]\$^\wedge\$\$[/\$]\$^\wedge A\hat{P}[/\$]\$^\wedge \hat{M}\tilde{f}_d + \dot{S} - \dot{\mu} + \tau_{d\Omega} \quad (74)$$

Although the control input V(t) is present in the open-loop error system, an additional derivative may be taken to facilitate the design of the RISE-based feedback controller. The closed-loop system may be expressed as:

$$J_\Omega \dot{r} = -\dot{J}_\Omega r + W^T \sigma'(U^T x_d) U^T \dot{x}_d - \hat{W}^T \sigma(\hat{U}^T x_d) - \quad (75)$$
$$\hat{W}^T \sigma'(\hat{U}^T x_d) \hat{U}^T \dot{x}_d - \hat{W}^T \sigma'(\hat{U}^T x_d) \dot{\hat{U}}^T x_d + \tilde{\epsilon}(x_d) + \dot{S} - \mu + \tau_{d\Omega}$$

where $$\sigma'(\hat{U}^T x_d) = \frac{d\sigma(U^T x_d)}{d(U^T x_d)} \bigg|_{U^T x_d = \hat{U}^T x_d}.$$

The following expression may then be obtained:

$$J_\Omega \dot{r} = -\dot{j}_\Omega r + \hat{W}^T \hat{\sigma}' \tilde{U}^T \dot{x}_d - \tilde{W}^T \hat{\sigma}' \hat{U}^T \dot{x}_d - \hat{W}^T \hat{\sigma}' \hat{U}^T \dot{x}_d -$$
$$W^T \hat{\sigma}' \hat{U}^T \dot{x}_d + W^T \sigma' U^T \dot{x}_d + \tilde{\epsilon}(x_d) - \hat{W}^T \hat{\sigma}' \dot{\hat{U}}^T x_d -$$
$$\dot{\hat{W}}^T \hat{\sigma} + \dot{S} - \mu + \tilde{\sigma}_{d\Omega} \quad (76)$$

Using the NN weight tuning laws, the expression may be rewritten as:

$$J_\Omega \dot{r} = -\frac{1}{2} \dot{J}_\Omega r + \tilde{N} + N - e_2 - (k_s + 1) r - \beta \mathrm{sgn}(e_2) \quad (77)$$

where unmeasurable auxiliary term $\tilde{N}$ may be defined as:

$$\tilde{N} = -\frac{1}{2} \dot{J}_\Omega r + \dot{S} + e_2 - \quad (78)$$
$$proj\big(\Gamma_1 \hat{\sigma}' \hat{U}^T \dot{x}_d e_2^T\big)^T \hat{\sigma} - \hat{W}^T \hat{\sigma}' proj\big(\Gamma_2 \dot{x}_d (\hat{\sigma}'^T \hat{W} e_2)^T\big)^T x_d$$

and unmeasurable auxiliary term N may be defined as:

$$N = N_B + N_d \quad (79)$$

$N_d$ may be defined as:

$$N_d = W^T \sigma' U^T \dot{x}_d + \dot{\tilde{\epsilon}}(x_d) + \dot{\tau}_{d\Omega} \quad (80)$$

and $N_B$ may be defined as:

$$N_B = N_{B_1} + N_{B_2} \quad (81)$$

where $N_{B_1}$ and $N_{B_2}$ may be given by:

$$N_{B_1} = -\hat{W}^T \hat{\sigma}' \tilde{\sigma}^T \dot{x}_d - W^T \hat{\sigma}' U^T \dot{x}_d \quad (82)$$

$$N_{B_2} = \hat{W}^T \sigma' \hat{U}^T \dot{x}_d + \tilde{W}^T \hat{\sigma}' \hat{U}^T \dot{x}_d \quad (83)$$

In some cases, it may be desirable to define the terms in such a way in order to segregate terms that are bounded by state-dependent bounds and terms that are upper bounded by constants for the development of the NN weight update laws and the subsequent stability analysis. The auxiliary term $N_B$ may be further segregated to develop gain conditions in the stability analysis. The mean value theorem may be applied to upper bound $\tilde{N}$ as:

$$|\tilde{N}| \leq \rho(\|z\|) \|z\| \quad (84)$$

where $z \triangleq [e_1 \ e_2 \ r]^T$ and the bounding function $\rho(\|z\|)$ is a positive, globally invertible, nondecreasing function. The following inequalities may be developed:

$$|N_d| \leq \zeta_1, \ |N_B| \leq \zeta_2, \ |\dot{N}_d| \leq \zeta_3, \ \text{and} \ |\dot{N}_B| \leq \zeta_4 + \zeta_5 |e_2| \quad (85)$$

where $\zeta_i$ for $i = 1, 2, \ldots 5$ are positive known constants.

The composite NN and RISE controller can ensure that all system signals are bounded under closed-loop operation and that the position tracking error is regulated in the sense that:

$$|e_1(t)| \to 0 \ \text{as} \ t \to \infty \quad (86)$$

provided the control gains are selected according to the following sufficient conditions:

$$\alpha_1 > \frac{1}{2}, \ \alpha_2 > \beta_2 + 1 \quad (87)$$
$$\beta_1 > \zeta_1 + \zeta_2 + \frac{1}{\alpha_2} \zeta_3 + \frac{1}{\alpha_2} \zeta_4, \ \beta_2 > \zeta_5$$

and control gain $k_s$ is selected sufficiently large based on the initial conditions of the error system.

Asynchronous Stimulation

NMES can sometimes lead to early onset of muscle fatigue during stimulation, limiting the duration that functional tasks can be performed in assistive devices. In some embodiments, a controller may apply asynchronous stimulation, which may reduce NMES-induced fatigue. Asynchronous stimulation generally refers to use of multiple stimulation channels and electrodes to target different muscles or different groups of motor units within a given muscle. Without wishing to be bound by a particular theory, asynchronous stimulation may lead to lower rates of fatigue due to reduced duty cycle (i.e., a lower average stimulation frequency) for the recruited motor units compared to conventional stimulation.

In some cases, switching between different muscles may introduce discontinuities in the open-loop dynamics. These discontinuities may be a consequence of the fact that the response to a given stimulus will differ for each subsystem (i.e., each subsystem activates a different number and/or type of muscle fibers). In certain embodiments, pulses may be delivered in an interleaved fashion to each stimulation channel. Utilizing interleaved pulses rather than sequentially delivering pulse trains may be advantageous, in some cases, at least in part because interleaving the pulses across the stimulation channels may provide an averaging effect due to the temporal summation of the force. The extent of the averaging effect may depend upon the stimulation frequency; higher stimulation frequencies may smooth the force output, but a primary motivation for utilizing interleaved pulses is to achieve decreased rates of fatigue through the use of low frequency stimulation.

As suggested by Equation 9 above, the joint dynamics during stimulation of two subsystems may be modeled as:

$$M_I + M_e + M_g + M_v + \tau_d = \tau_i + \tau_j \quad (88)$$

$\tau_i$ and $\tau_j$ represent the torque produced by stimulation of the $i^{th}$ and $j^{th}$ subsystems, and the inertial, gravitational, elastic, and viscous components are common to all subsystems since all subsystems act on the same joint. The unknown bounded disturbance torque $\tau_d$ may also be modeled as being common to all subsystems.

In some cases, the open-loop dynamics for asynchronous stimulation may be obtained as:

$$J \dot{r} = W - \tau_i - \tau_j + \tau_d, \ i \neq j \quad (89)$$

where J is the same inertia for each subsystem since each subsystem acts on the same joint complex. W ($\dot{e}_1$, $e_2$, t) denotes an auxiliary term defined as in Equation 17. The open-loop dynamics may be expressed as:

$$J \dot{r} = W - V_i \Omega_i - V_j \Omega_j + \tau_d \quad (90)$$

where $V_i$ denotes the stimulation applied to the $i^{th}$ subsystem by electrical stimulation, and $\Omega_i$ is a positive auxiliary term that relates the stimulation applied to the $i^{th}$ subsystem to the torque produced by the $i^{th}$ subsystem, defined as:

$$\Omega_i \triangleq \zeta_i \eta_i \cos a_i(q) \quad (91)$$

The first time derivative of $\Omega_i$ is continuous and bounded, and the second time derivative of $\Omega_i$ is bounded. In some cases, σ may denote a piecewise constant signal that selects the subsystem to be activated at time t. The instances when the value of σ changes are called the switching times, $t_i$. Immediately following each switching time, there may be a transition period Δt during which the input is transitioned from one subsystem to another. To facilitate the subsequent analysis, the closed-loop dynamics of the switched system and the Lyapunov candidate function may be made continuous through the signal X(t), where X is designed such that the transition period from one subsystem to another results in a continuous torque output due to stimulation. X denotes the percentage of the input delivered to one of the two selected subsystems, and the remaining percentage of the input (1−X), is delivered to the other subsystem. V(t) can denote the input to the system such that $V=V_i+V_j$, where $$V_i = XV, \quad V_j = (1-X)V. \tag{92}$$

The closed loop dynamics may be expressed as:

$$Jr = W - V\Omega_1 + \tau_d, \quad t_0 \leq t < t_1$$

$$Jr = W - XV\Omega_1 - (1-X)V\Omega_2 + \tau_d, \quad t_1 \leq t < t_2$$

$$Jr = W - XV\Omega_3 - (1-X)V\Omega_2 + \tau_d, \quad t_2 \leq t < t_3$$

$$Jr = W - XV\Omega_3 - (1-X)V\Omega_4 + \tau_d, \quad t_3 \leq t < t_4 \tag{93}$$

In some cases, an example definition of X may be given by:

$$X \triangleq \begin{cases} \dfrac{1 - \sin\!\left(\alpha(t - t_{2k-1}) - \dfrac{\pi}{2}\right)}{2}, & t \in [t_{2k-1}, t_{2k-1} + \Delta t) \\ 0, & t \in [t_{2k-1} + \Delta t, t_{2k}) \\ \dfrac{1 + \sin\!\left(\alpha(t - t_{2k-1}) - \dfrac{\pi}{2}\right)}{2}, & t \in [t_{2k}, t_{2k} + \Delta t) \\ 1, & t \in [t_0, t_1) \cup [t_{2k} + \Delta t, t_{2k+1}) \end{cases} \tag{94}$$

where X and its first time derivative are bounded and continuous and the second time derivative is bounded. The transition period in Equation 94 is defined as $$\Delta t \triangleq \frac{\pi}{a}$$

and may be made arbitrarily short through the choice of a.

In some cases, it may be desirable to obtain the time derivative of Equation 93 to facilitate stability analysis. The time derivative may be expressed as:

$$J\dot{r} = -\frac{1}{2}\dot{J}r + \tilde{N} + N_{d1} - e_2 + [XN_{d2,i} + (1-X)N_{d2,j}] - [X\Omega_i + (1-X)\Omega_j]\dot{V} + [\dot{X}N_{d3,i} - \dot{X}N_{d3,j}]V \tag{95}$$

where the following auxiliary terms may be defined as:

$$N \triangleq \dot{W} + e_2 - \left(\frac{1}{2}\dot{J}\right)_r + \tau_d \tag{96}$$

$$N_{d1} \triangleq J\ddot{q}_d + \dot{J}\dot{q}_d + \dot{M}_e + \dot{M}_g + \dot{M}_v + \tau_d \tag{97}$$

$$N_{d2,i} \triangleq -\dot{\Omega}_i V \tag{98}$$

$$N_{d3,i} \triangleq -\Omega_i \tag{99}$$

$$\tilde{N} \triangleq N - N_{d1}. \tag{100}$$

In some cases, it may be desirable to express the open-loop error system as in Equation 95 to separate the model into groups that are bounded by state-dependent bounds or by constants. By applying the Mean Value Theorem, Ñ may be upper bounded by state-dependent terms as:

$$|\tilde{N}| \leq \rho(\|z\|)\|z\| \tag{101}$$

where $z(t) \triangleq [e_1^T\ e_2^T\ r^T]^T$ and $\rho(\|z\|)$ is a positive, globally invertible, nondecreasing function. The desired trajectory may be used to prove the upper bounds:

$$|N_{d1}| \leq \zeta_{N_{d1}} \tag{102}$$

$$|\dot{N}_{d1}| \leq \zeta_{\dot{N}_{d1}} \tag{103}$$

$$|N_{d2,i}| \leq \rho_{N_{d2,i}}(\|z\|)|V(t)| \tag{104}$$

$$|\dot{N}_{d2,i}| \leq \rho_{1,\dot{N}_{d2,i}}(\|z\|)|V(t)| + \rho_{2,\dot{N}_{d2,i}}(\|z\|) \tag{105}$$

$$|N_{d3,i}| \leq \rho_{N_{d3,i}}(\|z\|) \tag{106}$$

$$|\dot{N}_{d3,i}| \leq \rho_{\dot{N}_{d3,i}}(\|z\|) \tag{107}$$

where $\zeta_{N_{d1}}$ and $\zeta_{\dot{N}_{d1}}$ are known positive constants and $\rho_{N_{2d,i}}(\|z\|)$, $\rho_{1,\dot{N}_{d2,i}}(\|z\|)$, $\rho_{2,\dot{N}_{d2,i}}(\|z\|)$, $\rho_{N_{d3,i}}(\|z\|)$, and $\rho_{\dot{N}_{d3,i}}(\|z\|)$ are positive, globally invertible, nondecreasing functions.

To facilitate stability analysis, Equation 95 may be expressed as:

$$J\dot{r} = -\frac{1}{2}\dot{J}r + \tilde{N} + N_{d1} - e_2 + \overline{N}_{d2} - \overline{\Omega}\dot{V} + \dot{X}\overline{N}_{d3}V \tag{108}$$

where $\overline{N}_{d2}$, $\overline{\Omega}$, and $\overline{N}_{d3}$ are continuous functions defined as:

$$\overline{N}_{d2} \triangleq [XN_{d2,i} + (1-X)N_{d2,j}] \tag{109}$$

$$\overline{N}_{d3} \triangleq [N_{d3,i} - N_{d3,j}] \tag{110}$$

$$\overline{\Omega} \triangleq [X\Omega_i + (1-X)\Omega_j] \tag{111}$$

The auxiliary terms may be bounded as:

$$|\overline{N}_{d2}| \leq \rho_{\overline{N}_{d2}}(\|z\|)|V(t)| \tag{112}$$

$$|\dot{\overline{N}}_{d2}| \leq \rho_{1,\overline{N}_{d2}}(\|z\|)|V(t)| + \rho_{2,\overline{N}_{d2}}(\|z\|) \tag{113}$$

$$|\overline{N}_{d3}| \leq \rho_{\overline{N}_{d3}}(\|z\|)|V(t)| \tag{114}$$

$$|\dot{\overline{N}}_{d3}| \leq \rho_{\overline{N}_{d3}}(\|z\|) \tag{115}$$

$$|\overline{\Omega}| \leq \rho_{\overline{\Omega}_0}(\|z\|) \tag{116}$$

$$|\dot{\overline{\Omega}}| \leq \rho_{\overline{\Omega}}(\|z\|). \tag{117}$$

The RISE-based voltage controller may be designed as:

$$V(t) \triangleq \frac{1}{\epsilon}(k_s + 1)(e_2(t) - e_2(0)) + v(t) \tag{118}$$

where v(t) is the generalized Fillipov solution to $$\dot{v}(t) = \frac{1}{\epsilon}(k_s + 1)\alpha_2 e_2(t) + (\beta + \beta_V|V|)\text{sgn}(e_2(t)) \quad (119)$$

where $\alpha_2$, $k_s$, $\beta$, $\beta_V$ are positive, constant control gains.

In some cases, the designed switching signal σ may have a finite number of discontinuities on any bounded time interval. Any two consecutive switching times, $t_i$ and $t_{i+1}$, may satisfy $t_i + \Delta t < t_{i+1}$, and the switching signal may remain constant for $t \in [t_i, t_{i+1})$.

The controller designed in Equation 108 may yield semi-global asymptotic tracking in the sense that $|e_1(t)| \to 0$ as $t \to \infty$ under any switching signal satisfying the condition above, provided that the control gains $\alpha_1$, $\alpha_2$, $k_s$, $\beta$, $\beta_V$ are selected according to the sufficient conditions:

$$\alpha_1 > \frac{1}{2}, k_s > \frac{\rho^2 \|y(0)\|}{4\lambda} \quad (120)$$

$$\beta_V > \max_{i \in S} \left\{ \frac{1}{\epsilon} \left[ \rho_{N_{d2,i}} + \left(\frac{\alpha}{2}\right)\rho_{N_{d3,i}} + 1 \right] \Big|_{\|z\| = \|y(0)\|} \right\} \quad (121)$$

$$\beta > \frac{1}{\epsilon}[\zeta_{N_{d1}} + 1] \quad (122)$$

$$\alpha_2 > \max\left\{ \left[\rho_{1,\tilde{N}_{d2}} + \rho_{2,\tilde{N}_{d2}}\beta_V + \rho_{\tilde{\Omega}}\beta_V^2 + \rho_{\tilde{\Omega}}\beta_V + \right. \right. \quad (123)$$
$$\left(\frac{\alpha}{2}\right)\rho_{\tilde{N}_{d3}}[1 + \alpha + \beta_V] + \left(\frac{\alpha}{2}\right)\rho_{\tilde{N}_{d3}}\right]\Big|_{\|z\|=\|y(0)\|},$$
$$\left[\zeta_{\tilde{N}_{d1}} + \left(\rho_{\tilde{\Omega}} + \rho_{2,\tilde{N}_{d2}} + \rho_{\tilde{\Omega}}\beta_V + \left(\frac{\alpha}{2}\right)\rho_{\tilde{N}_{d3}}\right)\beta + \right.$$
$$\left.\left. \frac{1}{\epsilon}(k_s+1)\|y(0)\|\left(\rho_{2,\tilde{N}_{d2}} + \rho_{\tilde{\Omega}}\beta_V + \left(\frac{\alpha}{2}\right)\rho_{\tilde{N}_{d3}}\right)\right]\Big|_{\|z\|=\|y(0)\|}, 2\right\}$$

where $\lambda \triangleq \min\{2\alpha_1 - 1, \alpha_2 - 1, 1\}$.

In some embodiments, the neural network may be used to estimate acceleration of a limb. A controller using such a neural network can achieve a controller using only position and velocity information.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. For example, various controllers and control algorithms were described. These controllers and control algorithms may be used together or separately, in any suitable combination. Those controllers and algorithms may be implemented in any suitable way, including as programs, stored in a computer readable medium, executed by a microcontroller or other suitable processing circuitry (such as an ASIC, FPGA or the like). When used together, these controllers may be implemented separately, with one serving to provide inputs to, or process outputs from, the other. Alternatively, they may be combined mathematically or logically, such that control equations, representing the combined controllers and algorithms, are derived before programming or implementation in control circuitry. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising," can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An orthotic device, comprising:
   one or more sensors;
   one or more electrodes;
   one or more elastic resistance elements configured to provide a resistance force or a compressive force against at least one body part of a person; and
   a nonlinear controller configured to:
      receive input signals from the one or more sensors,
      determine a current configuration of the orthotic device from a plurality of possible configurations of the orthotic device, the plurality of possible configurations of the orthotic device comprising a sitting configuration, a standing configuration, and a walking configuration,
      determine, using the one or more sensors, a range of motion and a desired trajectory associated with the at least one body part of the person,
      determine, using information associated with the range of motion, information associated with the desired trajectory, and information associated with the resistance force or the compressive force provided by the one or more elastic resistance elements, an amount of electrical stimulation to apply to the at least one body part of the person, and
      deliver said amount of electrical stimulation to the at least one body part of the person via at least one electrode.

2. The orthotic device of claim 1, wherein at least one of the sensors is an electrogoniometer configured to measure the angle between a first body part of a person and a second body part of a person coupled at a joint.

3. The orthotic device of claim 1, wherein at least one of the electrodes is configured to apply electrical stimulation to one or more body parts of a person.

4. The orthotic device of claim 1, wherein the controller generates the output signals as a nonlinear function of the input signals based at least in part on a determined parameter indicative of muscle fatigue.

5. An orthotic device, comprising:
   a bracing element configured to attach to a limb of a person;
   one or more sensors configured to measure the angle between a first body part of the person and a second body part of the person coupled at a joint;
   one or more electrodes configured to apply electrical stimulation to one or more body parts of the person;
   one or more elastic resistance elements coupled to said bracing element and configured to provide a resistance force or a compressive force against at least one of the first body part and the second body part of the person; and
   a nonlinear controller configured to:
      receive input signals from the one or more sensors,
      determine a current configuration of the orthotic device from a plurality of possible configurations of the orthotic device, the plurality of possible configurations of the orthotic device comprising a sitting configuration, a standing configuration, and a walking configuration,
      determine, using the one or more sensors, a range of motion and a desired trajectory associated with the at least one body part of the person,
      determine, using information associated with the range of motion, information associated with the desired trajectory, and information associated with the resistance force or the compressive force provided by the one or more elastic resistance elements, an amount of electrical stimulation to apply to the at least one body part of the person, and
      deliver said amount of electrical stimulation to the at least one body part of the person via at least one electrode.

6. The orthotic device of claim 5, wherein the nonlinear controller is configured to store at least one program.

7. The orthotic device of claim 6, wherein the at least one program corresponds to a functional activity.

8. The orthotic device of claim 7, wherein the activity comprises standing.

9. The orthotic device of claim 7, wherein the activity comprises walking.

10. The orthotic device of claim 6, wherein the program implements a control method that modulates the amplitude of the output signals.

11. The orthotic device of claim 6, wherein the program implements a control method that modulates the frequency of the output signals.

12. The orthotic device of claim 6, wherein the program implements a control method based at least in part on a value of a parameter indicative of muscle fatigue.

13. The orthotic device of claim 5, comprising at least two electrodes, wherein the nonlinear controller is configured to deliver interleaved output signals to the at least two electrodes.

14. The orthotic device of claim 5, wherein the controller is configured to record data from previous activities.

15. The orthotic device of claim 5, further comprising one or more elastic resistance elements, wherein at least one elastic resistance element comprises a spring and/or an elastic band.

16. The orthotic device of claim 5, further comprising a battery.

17. The orthotic device of claim 5, further comprising one or more sensors configured to measure velocity of the joint.

18. A method of providing functional electrical stimulation to a person, comprising:
   receiving signals from at least one sensor;
   determining a current configuration of an orthotic device from a plurality of possible configurations of said orthotic device, the plurality of possible configurations of the orthotic device comprising a sitting configuration, a standing configuration, and a walking configuration, the orthotic device comprising one or more elastic resistance elements configured to provide a resistance force or a compressive force against at least one body part of the person;

determining, using said at least one sensor, a range of motion and a desired trajectory associated with the at least one body part of the person;

determining, using information associated with the range of motion, information associated with the desired trajectory, and information associated with the resistance force or the compressive force provided by the one or more elastic resistance elements, an amount of electrical stimulation to apply to the at least one body part of the person; and delivering said amount of electrical stimulation to the at least one body part of the person via at least one electrode.

19. The method of claim 18, wherein the at least one sensor is an electrogoniometer configured to measure the angle between a first body part of a person and a second body part of a person coupled at a joint.

20. The method of claim 18, wherein the electrical stimulation assists the person in engaging in a functional activity.

21. The method of claim 20, wherein the functional activity comprises standing.

22. The method of claim 20, wherein the functional activity comprises walking.

23. The method of claim 18, wherein the calculating step comprises utilizing a closed-loop control method that achieves asymptotic stability or ultimately bounded tracking.

24. The method of claim 18, wherein the calculating step comprises tracking the time-varying trajectory of at least one body part of the person.

25. The method of claim 18, wherein the calculating step comprises utilizing a robust integral of the sign of the error (RISE) control method.

26. The method of claim 18, wherein the calculating step comprises utilizing a predictor-type control method that compensates for electromechanical delay.

27. The method of claim 18, wherein the calculating step comprises utilizing a control method comprising an adaptive feedforward method.

28. The method of claim 27, wherein the adaptive feedforward method comprises a neural network-based method.

* * * * *